United States Patent [19]

Inamine et al.

[11] 3,977,942

[45] Aug. 31, 1976

[54] FERMENTATION OF CEPHAMYCIN C

[75] Inventors: Edward Inamine, Rahway; Jerome Birnbaum, Morganville, both of N.J.

[73] Assignee: Merck & Co., Inc., Rahway, N.J.

[22] Filed: Nov. 21, 1975

[21] Appl. No.: 634,106

[52] U.S. Cl. .............................. 195/80 R; 195/36 C
[51] Int. Cl.² ............................................. C12D 9/00
[58] Field of Search ................... 195/36 C, 80 R, 29

[56] References Cited
UNITED STATES PATENTS

| | | | |
|---|---|---|---|
| 3,769,169 | 10/1973 | Birnbaum et al. | 195/80 R |
| 3,770,590 | 11/1973 | Inamine et al. | 195/80 R |
| 3,865,693 | 2/1975 | Arai et al. | 195/80 R |
| 3,886,044 | 5/1975 | Inamine et al. | 195/80 R |
| 3,914,158 | 10/1975 | Stapley et al. | 195/80 R |

*Primary Examiner*—Lionel M. Shapiro
*Attorney, Agent, or Firm*—Walter Patton; Julian S. Levitt

[57] ABSTRACT

Increased yields of the known and useful antibiotic cephamycin C [7-(D-5-amino-5-carboxyvaleramido)-3-(carbamoyloxymethyl)-7-methoxy-3-cephem-4-carboxylic acid] are obtained by the addition of D- or DL-arginine, D- or DL-ornithine and/or one of several polyamines; or D- or DL-lysine in combination with one of several polyamines to fermentation media composed of complex organic nutrients.

9 Claims, No Drawings

FERMENTATION OF CEPHAMYCIN C

SUMMARY OF THE INVENTION

This invention relates to an improved fermentation process for the production of the known and useful antibiotic cephamycin C [7-(D-5-amino-5-carboxyvaleramido)-3-carbamoyloxymethyl)-7-methoxy-3-cephem-4-carboxylic acid]. [Antimicrobial Agent and Chemotherapy, Vol. 2, September 1972, pages 121–131, 132–135, 281–286 and 287–290]. In particular, this invention relates to an improved method for the production of the antibiotic by fermentation of nutrient media with suitable strains of microorganisms such as, for example, Streptomyces.

The antibiotic is produced during the aerobic fermentation of suitable aqueous nutrient media under controlled conditions. Aqueous media such as those employed for the production of other antibiotics are suitable. Such media contain sources of carbon, nitrogen and inorganic salts which are assimilable by the microorganism. In addition, the fermentation media contain traces of metals necessary for the growth of the microorganism which are commonly supplied as impurities incidental to the other constituents of the medium. In general, carbohydrates such as sugars, for example, glucose, maltose, fructose, lactose, and the like, and starches such as grains, for example, oats and rye, corn starch, corn meal and the like can be used either alone or in combination as sources of assimilable carbon. The exact amount of the carbohydrate source or sources utilized in the medium will depend in part upon the other ingredients. It has been found, however, that an amount of carbohydrate between about 1 and 6 percent by weight of the medium is sufficient. A single carbon source may be used, or several carbon sources may be combined.

Satisfactory nitrogen sources include myriad proteinaceous materials such as various forms of hydrolysates of casein, soybean meal, corn steep liquor, distillers solubles, yeast products, tomato paste, and the like. The various sources of nitrogen can be used either alone or in combination, and are used in amounts ranging from 0.2–6 percent by weight of the aqueous medium.

The fermentation is carried out at temperatures ranging from 20° to 37°C., however, for optimum results, it is preferable to conduct the fermentation at temperatures of from about 24° to 32°C. The pH of the nutrient mediums suitable for growing the Streptomyces cultures and producing the antibiotic should be in the range of from about 6.0 to 8.0.

Cephamycin C is produced during the aerobic fermentation described above by a strain of *Streptomyces lactamdurans* capable of producing said compound as, for example, by the strain on deposit in the culture collection of the Northern Utilization Research and Development Branch of the U.S. Department of Agriculture at Peoria, Illinois under accession number NRRL 3802. Other strains of this species, such as mutants obtained by mutating agents or isolated from nature, can also be used.

Cephamycin C and its salts demonstrate resistance not only to penicillinase but to the cephalosporinases as well. This compound is active in inhibiting the growth of gram-positive and gram-negative microorganisms. Unlike cephalosporin C which has relatively low antibacterial activity, cephamycin C exhibits a significant in vivo gram-negative effect with a potency which, in general, is greater than cephalothin. This activity includes effectiveness against the following gram-negative bacteria: *Escherichia coli, Proteus vulgaris, Proteus mirabilis, Salmonella schottmuelleri, Klebsiella pneumoniae AD, Klebsiella pneumoniae B,* and *Paracolonbacterium arizonae.*

Bioassays for the antibiotic cephamycin C are run by a disc-plate procedure using 3/8 inch filter paper discs, in accordance with the procedure described in U.S. Pat. Nos. 3,769,169; 3,770,590 and 3,886,044 the contents of which are incorporated herein by reference. The assay plates are prepared using Difco nutrient agar plus 2.0 g./l. Difco yeast extract at 10 ml. per plate. An overnight growth of the assay organism, *Vibrio percolans* ATCC 8461 is diluted in sterile saline solution to a suspension having 40 percent transmittance at a wave length of 660 m$\mu$. This suspension is added at 20 ml./liter of medium prior to pouring the plates.

The assay plates are held at 4°C. until used (5 day maximum). Following the application of the antibiotic-saturated assay discs the plates are incubated at 28°C. for a period of from 8 to 24 hours. Zones of inhibition are read as mm. diameter. They are used to determine relative potencies or, when compared with a purified reference standard of cephamycin C, the potency in $\mu$g/ml.

Due to the inherent difficulty in separating pure cephamycin C from the large quantities of impurities in the fermentation broth, it is of considerable importance to find a way to increase the concentration of the antibiotic relative to the total broth solids.

It is, therefore, an object of this invention to provide a method of increasing the yield of antibiotic in a fermentation process. It is a further object of the invention to provide a method of increasing the yield of an antibiotic using relatively inexpensive, readily available chemical additives in the fermentation process. Further objects of the invention will become apparent.

It has been discovered that the addition of D- or DL-arginine, D- or DL-ornithine or one of several polyamines such as 1,3-diaminopropane; 1,3-diamino-2-2-hydroxypropane; N-methyl-1,3-diaminopropane, agmatine, spermidine, spermine, cadaverine and putrescine to complex organic fermentation media will enhance the production of cephamycin C. Furthermore, the amino acids D- or DL-arginine, D- or DL-ornithine or D- or DL-lysine can also be added in combination with a polyamine such as 1,3-diaminopropane; 1,3-diamino-2-hydroxypropane; N-methyl-1,3-diaminopropane, agmatine, spermidine, spermine, cadaverine and putrescine to further improve the fermentation yield.

By "complex organic" media is meant media wherein some of the ingredients are not chemically defined. An example of such media is one consisting of distillers solubles, primary dried yeast, glycerol, dimethylformamide, glycine, L-phenylalanine, sodium thiosulfate and a defoamer wherein distillers solubles and primary dried yeast are not chemically defined.

The amount of the amino acid and/or polyamine needed to stimulate production of the antibiotic cephamycin C is to some extent dependent upon both the culture and the medium employed. In the case of the *Streptomyces lactamdurans* culture an increase in the production of the antibiotic cephamycin C, has been observed in a complex organic media containing from about 0.025 to about 0.40 percent (weight/volume) of the amino acid D- or DL-arginine or D- or DL-ornithine calculated as the hydrochloride; or from about 0.01 to about 0.2% (weight/volume) of 1,3-diaminopropane calculated as the dihydrochloride; or from about 0.0025 to 0.05% (weight/volume) of spermidine or spermine calculated as the trihydrochloride and tetrahydrochloride respectively; or from about 0.025 to 0.2% (weight/volume) of cadaverine or putrescine calculated as the dihydrochloride; or from about 0.025 to 0.2% (weight/volume) of agmatine calculated as the sulfate; or from about 0.05 to about 0.2% (weight/volume) of 1,3-diamino-2-hydroxypropane or N-methyl-1,3-diaminopropane as the free base.

In addition to being used singly, the amino acids and polyamines may be combined to afford an additive that will stimulate the yield of cephamycin C in complex organic nutrient media employing *Streptomyces lactamdurans*. The combined additions of the amino acids (arginine, lysine and ornithine) and the polyamines are shown to increase cephamycin C productivity to a greater extent than when the compounds are added separately.

An increase in the production of the antibiotic has also been observed by adding the amino acids D- or DL-arginine, D- or DL-ornithine or D- or DL-lysine wherein the amino acid is present to the extent of about 0.1 to about 0.2% (weight/volume) calculated as the hydrochloride in combination with about 0.1% (weight/volume) of 1,3-diaminopropane or cadaverine or putrescine calculated as the dihydrochloride; or about 0.02% (weight/volume) of spermidine or spermine calculated as the trihydrochloride and tetrahydrochloride respectively; or about 0.1% (weight/volume) agmatine calculated as the sulfate; or about 0.05 to about 0.2% (weight/volume) 1,3-diamino-2-hydroxypropane or N-methyl-1,3-diaminopropane as the free base. Optimum yields of antibiotic are obtained wherein the media contains amino acids to the extent of about 0.1 percent to about 0.2 percent and polyamine compounds to the extent of about 0.1 percent with the exception of spermidine and spermine which are most effective at a level of about 0.02 percent. The preferred combination of amino acid and polyamine is DL-lysine and 1,3-diaminopropane added to the extent of about 0.1% (weight/volume) calculated as the hydrochloride and dihydrochloride, respectively.

One skilled in the art will appreciate that in addition to employing said amino acids and polyamines, salts of these materials may be utilized in the practice of the invention. For example, the —HCl, —SO$_4$ and —PO$_4$ salts may be employed in the basal production medium to increase the yield of antibiotic.

The time of addition of the yield-increasing additives to the fermentation batch is not critical. Thus, the addition may take place at the time of inoculation with the Streptomyces culture to as long as 72 hours subsequent. In general, it is preferred to add the amino acids and polyamines just prior to the time of inoculation.

The above discussion and examples below are primarily directed to fermentations using a particular strain of the *Streptomyces lactamdurans* culture. However, other strains of this organism such as mutants can also be used to produce the antibiotic and it should be obvious to one skilled in the art that following the teaching of this invention, the yield of antibiotic can be increased by the addition of D- or DL-arginine, D- or DL-ornithine and/or a polyamine; or D- or DL-lysine in combination with a polyamine to the fermentation broth containing such strains. Following the teaching of this invention obvious modifications or changes in the optimal levels of the additive or the time of addition to the fermentation medium will be within the skill of the artisan, no matter which strain of *Streptomyces lactamdurans* is used to produce the antibiotic cephamycin C.

Although the antibiotic cephamycin C is produced by both surface and submerged cultures, it is presently preferred to carry out the fermentation in the submerged state. Small scale fermentations are conveniently carried out by placing suitable quantities of nutrient medium in flasks, sterilizing the flasks and contents by heating to 120°C., inoculating the flasks with either spores or a vegetative cellular growth of a cephamycin C producing strain of Streptomyces, loosely stoppering the necks of the flasks with cotton, and permitting the fermentation to proceed at a constant temperature of about 28°C. on a shaker for 1 to 4 days.

For larger scale work, it is preferable to conduct the fermentation in suitable tanks provided with an agitator and a means for aerating the fermentation medium. In this method, the nutrient medium is made up in the tank and sterilized by heating at 120°C. After cooling the sterilized medium is inoculated with a suitable source of vegetative cellular growth of the Streptomyces culture and the fermentation is permitted to proceed for 3–5 days while agitating and/or aerating the nutrient medium and maintaining the temperature at about 28°C. This method of producing cephamycin C is particularly suited for the preparation of large quantities of the antibiotic.

In carrying out the invention, a cell suspension is prepared by the addition of sterile medium to an agar slant culture of the cephamycin C producing microorganism. Growth from the slant culture is suspended in the medium and the suspension then used to inoculate a seed flask and the seed flask is shaken at about 28°C. for 1–3 days in order to obtain good growth. The seed flask is then used to inoculate the production flasks. Alternatively, the seed flask can be inoculated from a lyophilized culture or a frozen inoculum and also more than one seed stage may be used.

The basal production medium is made up in deionized water, adjusted to about pH 7, dispensed into production flasks and sterilized by autoclaving for about 20 minutes. The desired concentration of sterile additive is added to the production flasks and inoculation is generally carried out using about 1 ml. per 40 ml. of production medium. The fermentation is permitted to proceed for 2–4 days while agitating and/or aerating the nutrient medium and maintaining the temperature at about 28°C. All of the production flasks, i.e., those containing the additives recited above and the flasks used as controls, are then assayed, generally after 96 hours, to determine the amount of antibiotic produced in each flask.

Aliquots from the production flasks are assayed by diluting the sample in 0.02 molar phosphate buffer at pH 7 to an appropriate concentration. The test organism is *Vibrio percolans* ATCC 8461, and the assay medium is Difco nutrient agar plus 0.2 percent Difco yeast extract. Discs of ⅜ inch diameter are dipped into a solution containing 5 $\mu$g. per milliliter of the standard antibiotic and are placed on the plate in a position alternate to the samples to be tested. The plates are then incubated at 28°C. for 18 hours, and the zone diameters in millimeters are determined. Five standard discs containing 4 levels of the standard antibiotic ranging from 2.5 to 20 µg/ml. are employed. The quantity of antibiotic in the test sample is calculated by means of the standard curve prepared from the known concentrations of the standard antibiotic solutions. The results are reported in terms of µg per milliliter of the antibiotic in the form of the free acid.

The antibiotic can be recovered from the fermentation medium by a number of procedures. The filtered broth can be passed through one or more ion exchange columns. The amphoteric nature of the antibiotic enables selection of both cationic and anionic ion exchange resins to optimize recovery. The adsorbed antibiotic can then be removed by elution, preferably in a volatile solvent such as pyridine which can be easily removed.

The following examples are given for purposes of illustration and not by way of limitation.

EXAMPLE 1

Preparation of Inoculum

A lyophilized tube of *Streptomyces lactamdurans* NRRL 3802 is opened aseptically and its contents transferred to 40 ml. of sterile medium contained in a 250 ml. baffled Erlenmeyer flask wherein the medium contains 10 g/l. Primary Dried Yeast, N.F. at pH 7 (supplied by Yeast Products Co., Paterson, N.J.) in deionized water. The flask is incubated at 28°C. on a rotary shaker (2-inch displacement) set at 220 rpm, for 48 hours, at which time luxuriant growth of the organism is apparent. Aliquots of the flask contents are dispensed into sterile tubes and stored at −78°C. until used.

First Seed Stage

The frozen inoculum is thawed at 36°C. and 1 ml. is used to inoculate 40 ml. of sterile medium containing 10 g./l. Primary Dried Yeast, N.F. at pH 7 (supplied by Yeast Products Co., Paterson, N.J.) in deionized water in a 250 ml. baffled Erlenmeyer flask. The organism is incubated at 28°C. on a rotary shaker (2-inch displacement) set at 220 rpm, for about 45 hours.

Second Seed Stage

One ml. of the first stage seed is used to inoculate 40 ml. of sterile medium containing 1% Ardamine YEP Yeast Autolysate (supplied by Yeast Products Co., Paterson, N.J.) in deionized water at pH 7 in a 250 ml. baffled Erlenmeyer flask. The organism is incubated at 28°C. on a rotary shaker (2-inch displacement) at 220 rpm for 24 hours and serves as the inoculum for the production medium.

Basal Production Medium

The basal production medium has the following composition:

|  | (%) |
|---|---|
| Distillers Solubles | 3.0 w/v |
| Primary Dried Yeast N.F. | 0.75 w/v |
| Glycerol | 1.25 w/v |
| Dimethylformamide | 1.0 v/v |
| Glycine | 0.05 w/v |
| L-phenylalanine | 0.3 w/v |
| Mobil Par S-Defoamer | 0.25 w/v |
| Sodium Thiosulfate* | 0.1 w/v |

*Added asceptically at 0–24 hours post-inoculation from a filter sterilized concentrated stock solution to give the final concentration as shown.

The medium is made up in deionized water, adjusted to pH 7 with sodium hydroxide; 40 ml. portions are dispensed into 250 ml. Erlenmeyer flasks and sterilized by autoclaving for 20 minutes and cooled.

To a series of flasks, prepared as described above, is added D- or DL-arginine.HCl, D- or DL-ornithine.HCl. The flasks are identical in every way except for the presence of the amino acid.

Concentrated stock solutions of the amino acid additives are prepared in water and neutralized with either hydrochloric acid or sodium hydroxide to pH 7. The filter sterilized stock solutions are added to the flasks containing the basal production medium at the desired final concentrations just prior to inoculation with the organism.

After the addition of the amino acid additives, the medium is inoculated with 2.5% by volume of the second stage seed and incubated for 96 hours at 28°C. on a rotary shaker (2-inch displacement) set at 220 rpm. After completion of the fermentation the cells are removed by centrifugation and the clarified broth assayed for cephamycin C in the manner described above with *Vibrio percolans* ATCC 8461 as the test organism.

TABLE 1

| Additives to Basal Production Medium | Concentration of Additives (%) to Basal Production Medium | | | | | | |
|---|---|---|---|---|---|---|---|
|  | 0 | 0.025 | 0.05 | 0.10 | 0.20 | 0.30 | 0.40 |
|  | Cephamycin C Production (µg/ml.) | | | | | | |
| None (Control) | 199 |  |  |  |  |  |  |
| D-Arginine HCl |  | 202 | 232 | 282 | 234 | 264 | — |
| D-Ornithine.HCl |  | 230 | 229 | 221 | 264 | 246 | — |
| DL-Ornithine.HCl |  | 212 | 218 | 199 | 246 | 301 | — |
| None (Control) | 162 |  |  |  |  |  |  |
| D-Arginine.HCl |  | — | 238 | 206 | 196 | — | 193 |
| DL-Arginine.HCl |  | — | 200 | 193 | 215 | — | 246 |
| D-Ornithine.HCl |  | — | 224 | 232 | 222 | — | 254 |
| DL-Ornithine.HCl |  | — | 185 | 202 | 187 | — | 168 |
| None (Control) | 172 |  |  |  |  |  |  |
| D-Arginine.HCl |  | — | 268 | 235 | 219 | — | 210 |
| DL-Arginine.HCl |  | — | 209 | 219 | 223 | — | 200 |
| D-Ornithine.HCl |  | — | 218 | 216 | 230 | — | 251 |
| DL-Ornithine.HCl |  | — | 191 | 222 | 270 | — | 288 |
| None (Control) | 160 |  |  |  |  |  |  |
| D-Arginine.HCl |  | 215 | 232 | 239 | 247 | — | — |
| DL-Arginine.HCl |  | 226 | 218 | 237 | 259 | — | — |
| D-Ornithine.HCl |  | — | 202 | 221 | 301 | — | 304 |
| DL-Ornithine.HCl |  | — | 201 | 201 | 232 | — | 250 |

EXAMPLE 2

Preparation of Inoculum

A lyophilized tube of *Streptomyces lactamdurans* NRRL 3802 is opened asceptically and its contents transferred to 40 ml. of sterile medium contained in a 250 ml. baffled Erlenmeyer flask wherein the medium contains 10 g./l. Primary Dried Yeast, N.F. at pH 7 (supplied by Yeast Products Co., Paterson, N.J.) in deionized water. The flask is incubated at 28°C. on a rotary shaker (2-inch displacement) set at 220 rpm, for 48 hours, at which time luxuriant growth of the organism is apparent. Aliquots of the flask contents are dispensed into sterile tubes and stored at −78°C. until used.

First Seed Stage

The frozen inoculum is thawed at 36°C. and 1 ml. is used to inoculate 40 ml. of sterile medium containing 10 g./l. Primary Dried Yeast, N.F. at pH 7 (supplied by Yeast Products Co., Paterson, N.J.) in deionized water in a 250 ml. baffled Erlenmeyer flask. The organism is incubated at 28°C. on a rotary shaker (2-inch displacement) set at 220 rpm, for 45 hours.

Second Seed Stage

One ml. of the first stage seed is used to inoculate 40 ml. of sterile medium containing 1% Ardamine YEP Yeast Autolysate (supplied by Yeast Products Co., Paterson, N.J.) in deionized water at pH 7 in a 250 ml. baffled Erlenmeyer flask. The organism is incubated at 28°C. on a rotary shaker (2-inch displacement) at 220 rpm for 24 hours and serves as the inoculum for the production medium.

Basal Production Medium

The basal production medium has the following composition:

|  | (%) |
|---|---|
| Distillers Solubles | 3.0 w/v |
| Primary Dried Yeast N.F. | 0.75 w/v |
| Glycerol | 1.25 w/v |
| Dimethylformamide | 1.0 v/v |
| Glycine | 0.05 w/v |
| L-phenylalanine | 0.3 w/v |
| Mobil Par S-Defoamer | 0.25 w/v |
| Sodium Thiosulfate* | 0.1 w/v |

*Added asceptically at 0–24 hours post-inoculation from a filter sterilized concentrated stock solution to give the final concentration as shown.

The medium is made up in deionized water, adjusted to pH 7 with sodium hydroxide; 40 ml. portions are dispensed into 250 ml. Erlenmeyer flasks and sterilized by autoclaving for 20 minutes and cooled.

To a series of flasks, prepared as described above, is added 1,3-diaminopropane.2HCl; agmatine sulfate; spermidine.3HCl; spermine:4HCl; cadaverine.2HCl; putrescine.2HCl; 1,3-diamino-2-hydroxypropane and N-methyl-1,3-diaminopropane. The flasks are identical in every way except for the presence of the amino acid.

Concentrated stock solutions of the polyamine additives are prepared in water and neutralized with either hydrochloric acid or sodium hydroxide to pH 7. The filter sterilized stock solutions are added to the flasks containing the basal production medium at the desired final concentrations just prior to inoculation with the organism.

After the addition of the polyamine additives, the medium is inoculated with 2.5% by volume of the second stage seed and incubated for 96 hours at 28°C. on a rotary shaker (2-inch displacement) set at 220 rpm. After completion of the fermentation the cells are removed by centrifugation and the clarified broth assayed for cephamycin C in the manner described above with *Vibrio percolans* ATCC 8461 as the test organism.

TABLE 2

| Additives to Basal Production Medium | Concentration of Additives (%) to Basal Production Medium ||||||||| 
|---|---|---|---|---|---|---|---|---|---|
|  | 0 | 0.0025 | 0.005 | 0.010 | 0.020 | 0.025 | 0.05 | 0.10 | 0.20 |
|  | Cephamycin C Production (μg/ml.) |||||||||
| None (Control) | 200 |  |  |  |  |  |  |  |  |
| 1,3-Diaminopropane.2HCl |  | — | — | 237 | — | 263 | 282 | 290 | — |
| Agmatine Sulfate |  | — | — | — | — | 202 | 247 | 257 | 235 |
| Spermidine.3HCl |  | — | 262 | 304 | 315 | — | 320 | — | — |
| Spermine.4HCl |  | 197 | 278 | 275 | — | — | — | — | — |
| None (Control) | 165 |  |  |  |  |  |  |  |  |
| 1,3-Diaminopropane.2HCl |  | — | — | 198 | — | 232 | 330 | 309 | — |
| Spermidine.3HCl |  | 219 | 230 | 255 | 282 | — | — | — | — |
| Spermine.4HCl |  | — | 234 | 341 | 296 | — | 318 | — | — |
| Cadaverine.2HCl |  | — | — | — | — | 224 | 244 | 255 | 272 |
| None (Control) | 199 |  |  |  |  |  |  |  |  |
| 1,3-Diaminopropane.2HCl |  | — | — | 263 | — | 299 | 332 | 368 | 344 |
| Agmatine Sulfate |  | — | — | — | — | 288 | 215 | 219 | 215 |
| Spermidine.3HCl |  | 285 | 331 | 387 | 361 | — | 248 | — | — |
| Spermine.4HCl |  | 276 | 282 | 369 | 494 | — | 377 | — | — |
| Cadaverine.2HCl |  | — | — | — | — | 226 | 258 | 271 | 254 |
| Putrescine.2HCl |  | — | — | — | — | 272 | 265 | 276 | 284 |
| None (Control) | 170 |  |  |  |  |  |  |  |  |
| 1,3-Diamino-2-hydroxypropane |  | — | — | — | — | — | 184 | 203 | 199 |
| N-Methyl-1,3-diaminopropane |  | — | — | — | — | — | 226 | 192 | 202 |

EXAMPLE 3

Preparation of Inoculum

A lyophilized tube of *Streptomyces lactamdurans* NRRL 3802 is opened asceptically and its contents transferred to 40 ml. of sterile medium contained in a 250 ml. baffled Erlenmeyer flask wherein the medium contains 10 g./l. Primary Dried Yeast, N.F. at pH 7 (supplied by Yeast Products Co., Paterson, N.J.) in deionized water. The flask is incubated at 28°C. on a rotary shaker (2-inch displacement) set at 220 rpm, for 48 hours, at which time luxuriant growth of the organism is apparent. Aliquots of the flask contents are dispensed into sterile tubes and stored at −78°C. until used.

First Seed Stage

The frozen inoculum is thawed at 36°C. and 1 ml. is used to inoculate 40 ml. of sterile medium containing 10 g./l. Primary Dried Yeast, N.F. at pH 7 (supplied by Yeast Products Co., Paterson, N.J.) in deionized water in a 250 ml. baffled Erlenmeyer flask. The organism is incubated at 28°C. on a rotary shaker (2-inch displacement) set at 220 rpm, for about 45 hours.

Second Seed Stage

One ml. of the first stage seed is used to inoculate 40 ml. of sterile medium containing 1% Ardamine YEP Yeast Autolysate (supplied by Yeast Products Co., Paterson, N.J.) in deionized water at pH 7 in a 250 ml. baffled Erlenmeyer flask. The organism is incubated at 28°C. on a rotary shaker (2-inch displacement) at 220 rpm for 24 hours and serves as the inoculum for the production medium.

Basal Production Medium

The basal production medium has the following composition:

|   | (%) |
|---|---|
| Distillers Solubles | 3.0 w/v |
| Primary Dried Yeast N.F. | 0.75 w/v |
| Glycerol | 1.25 w/v |
| Dimethylformamide | 1.0 v/v |
| Glycine | 0.05 w/v |
| L-phenylalanine | 0.3 w/v |
| Mobil Par S-Defoamer | 0.25 w/v |
| Sodium Thiosulfate* | 0.1 w/v |

*Added asceptically at 0–24 hours post-inoculation from a filter sterilized concentrated stock solution to give the final concentration as shown.

The medium is made up in deionized water, adjusted to pH 7 with sodium hydroxide; 40 ml. portions are dispensed into 250 ml. Erlenmeyer flasks and sterilized by autoclaving for 20 minutes and cooled.

To a series of flasks, prepared as described above, is added D- or DL-lysine.HCl, D-arginine.HCl, D-ornithine.HCl and/or 1,3-diaminopropane.2HCl. The flasks are identical in every way except for the presence of the amino acid.

Concentrated stock solutions of the additives are prepared in water and neutralized with either hydrochloric acid or sodium hydroxide to pH 7. The filter sterilized stock solutions are added to the flasks containing the basal production medium at the desired final concentrations just prior to inoculation with the organism.

After the addition of the additives, the medium is inoculated with 2.5% by volume of the second stage seed and incubated for 96 hours at 28°C. on a rotary shaker (2-inch displacement) set at 220 rpm. After completion of the fermentation the cells are removed by centrifugation and the clarified broth assayed for cephamycin C in the manner described above with *Vibrio percolans* ATCC 8461 as the test organism.

TABLE 3

| Additives to Basal Production Medium | Concentration of 1,3-Diaminopropane.2HCl Added to Basal Production Medium (%) | |
|---|---|---|
| | 0 | 0.10% |
| | Cephamycin C Production (μg/ml.) | |
| None | 129 | 235 |
| D-Lysine.HCl, 0.1% | 182 | 286 |
| DL-Lysine.HCl, 0.1% | 152 | 264 |
| D-Arginine.HCl, 0.1% | 173 | 243 |
| D-Ornithine.HCl, 0.1% | 188 | 282 |

EXAMPLE 4

Preparation of Inoculum

A lyophilized tube of *Streptomyces lactamdurans* NRRL 3802 is opened asceptically and its contents transferred to 40 ml. of sterile medium contained in a 250 ml. baffled Erlenmeyer flask wherein the medium contains 10 g./l. Primary Dried Yeast, N.F. at pH 7 (supplied by Yeast Products Co., Paterson, N.J.) in deionized water. The flask is incubated at 28°C. on a rotary shaker (2-inch displacement) set at 220 rpm, for 48 hours, at which time luxuriant growth of the organism is apparent. Aliquots of the flask contents are dispensed into sterile tubes and stored at −78°C. until used.

First Seed Stage

The frozen inoculum is thawed at 36°C. and 1 ml. is used to inoculate 40 ml. of sterile medium containing 10 g./l. Primary Dried Yeast, N.F. at pH 7 (supplied by Yeast Products Co., Paterson, N.J.) in deionized water in a 250 ml. baffled Erlenmeyer flask. The organism is incubated at 28°C. on a rotary shaker (2-inch displacement) set at 220 rpm, for 45 hours.

Second Seed Stage

One ml. of the first stage seed is used to inoculate 40 ml. of sterile medium containing 1% Ardamine YEP Yeast Autolysate (supplied by Yeast Products Co., Paterson, N.J.) in deionized water at pH 7 in a 250 ml. baffled Erlenmeyer flask. The organism is incubated at 28°C. on a rotary shaker (2-inch displacement) at 220 rpm for 24 hours and serves as the inoculum for the production medium.

Basal Production Medium

The basal production medium has the following composition:

|   | (%) |
|---|---|
| Distillers Solubles | 3.0 w/v |
| Primary Dried Yeast N.F. | 0.75 w/v |
| Glycerol | 1.25 w/v |
| Dimethylformamide | 1.0 v/v |
| Glycine | 0.05 w/v |
| L-phenylalanine | 0.3 w/v |
| Mobil Par S-Defoamer | 0.25 w/v |

| | (%) |
|---|---|
| Sodium Thiosulfate* | 0.1 w/v |

*Added asceptically at 0–24 hours post-inoculation from a filter sterilized concentrated stock solution to give the final concentration as shown.

The medium is made up in deionized water, adjusted to pH 7 with sodium hydroxide; 40 ml. portions are dispensed into 250 ml. Erlenmeyer flasks and sterilized by autoclaving for 20 minutes and cooled.

To a series of flasks, prepared as described above, is added D- or DL-lysine.HCl; 1,3-diamino-2-hydroxypropane and N-methyl-1,3-diaminopropane. The flasks are identical in every way except for the presence of the amino acid.

Concentrated stock solutions of the additives are prepared in water and neutralized with either hydrochloric acid or sodium hydroxide to pH 7. The filter sterilized stock solutions are added to the flasks containing the basal production medium at the desired final concentrations just prior to inoculation with the organism.

After the addition of the additives, the medium is inoculated with 2.5% by volume of the second stage seed and incubated for 96 hours at 28°C. on a rotary shaker (2-inch displacement) set at 220 rpm. After completion of the fermentation the cells are removed by centrifugation and the clarified broth assayed for cephamycin C in the manner described above with *Vibrio percolans* ATCC 8461 as the test organism.

TABLE 4

| Additives to Basal Production Medium | Additives to Basal Production Medium | | | |
|---|---|---|---|---|
| | None | D-Lysine.HCl 0.1% | DL-Lysine.HCl 0.1% | DL-Lysine.HCl 0.2% |
| | Cephamycin C Production (μg/ml.) | | | |
| None | 154 | 234 | 169 | 150 |
| 1,3-Diamino-2-hydroxypropane, 0.05% | 222 | 264 | 311 | 240 |
| 1,3-Diamino-2-hydroxypropane, 0.10% | 229 | 276 | 333 | 255 |
| 1,3-Diamino-2-hydroxypropane, 0.20% | 246 | 355 | — | — |
| N-Methyl-1,3-diaminopropane, 0.05% | 248 | 285 | 311 | 255 |
| N-Methyl-1,3-diaminopropane, 0.10% | 189 | 307 | 304 | 271 |
| N-Methyl-1,3-diaminopropane, 0.20% | 151 | 247 | — | — |

EXAMPLE 5

Preparation of Inoculum

A lyophilized tube of *Streptomyces lactamdurans* NRRL 3802 is opened asceptically and its contents transferred to 40 ml. of sterile medium contained in a 250 ml. baffled Erlenmeyer flask wherein the medium contains 10 g./l. Primary Dried Yeast, N.F. at pH 7 (supplied by Yeast Products Co., Paterson, N.J.) in deionized water. The flask is incubated at 28°C. on a rotary shaker (2-inch displacement) set at 220 rpm, for 48 hours, at which time luxuriant growth of the organism is apparent. Aliquots of the flask contents are dispensed into sterile tubes and stored at −78°C. until used.

First Seed Stage

The frozen inoculum is thawed at 36°C. and 1 ml. is used to inoculate 40 ml. of sterile medium containing 10 g./l. Primary Dried Yeast, N.F. at pH 7 (supplied by Yeast Products Co., Paterson, N.J.) in deionized water in a 250 ml. baffled Erlenmeyer flask. The organism is incubated at 28°C. on a rotary shaker (2-inch displacement) set at 220 rpm, for 45 hours.

Second Seed Stage

One ml. of the first stage seed is used to inoculate 40 ml. of sterile medium containing 1% Ardamine YEP Yeast Autolysate (supplied by Yeast Products Co., Paterson, N.J.) in deionized water at pH 7 in a 250 ml. baffled Erlenmeyer flask. The organism is incubated at 28°C. on a rotary shaker (2-inch displacement) at 220 rpm for 24 hours and serves as the inoculum for the production medium.

Basal Production Medium

The basal production medium has the following composition:

| | (%) |
|---|---|
| Distillers Solubles | 3.0 w/v |
| Primary Dried Yeast N.F. | 0.75 w/v |
| Glycerol | 1.25 w/v |
| Dimethylformamide | 1.0 v/v |
| Glycine | 0.05 w/v |
| L-phenylalanine | 0.3 w/v |
| Mobil Par S-Defoamer | 0.25 w/v |
| Sodium Thiosulfate* | 0.1 w/v |

*Added asceptically at 0–24 hours post-inoculation from a filter sterilized concentrated stock solution to give the final concentration as shown.

The medium is made up in deionized water, adjusted to pH 7 with sodium hydroxide; 40 ml. portions are dispensed into 250 ml. Erlenmeyer flasks and sterilized by autoclaving for 20 minutes and cooled.

To a series of flasks, prepared as described above, is added D- or DL-lysine.HCl; agmatine sulfate; cadaverine.HCl; 1,3-diaminopropane.2HCl; putrescine.2HCl; spermidine.3HCl and spermine.4HCl. The flasks are identical in every way except for the presence of the amino acid.

Concentrated stock solutions of the additives are prepared in water and neutralized with either hydrochloric acid or sodium hydroxide to pH 7. The filter sterilized stock solutions are added to the flasks containing the basal production medium at the desired final concentrations just prior to inoculation with the organism.

After the addition of the additives, the medium is inoculated with 2.5% by volume of the second stage seed and incubated for 96 hours at 28°C. on a rotary shaker (2-inch displacement) set at 220 rpm. After completion of the fermentation the cells are removed by centrifugation and the clarified broth assayed for cephamycin C in the manner described above with *Vibrio percolans* ATCC 8461 as the test organism.

TABLE 5

| Additives to Basal Production Medium | | | | | |
|---|---|---|---|---|---|
| Additives to Basal Production Medium | None | D-Lysine.HCl 0.1% | D-Lysine.HCl 0.2% | DL-Lysine.HCl 0.1% | DL-Lysine.HCl 0.2% |
| | Cephamycin C Production (μg/ml.) | | | | |
| None | 171 | 242 | 301 | 157 | 184 |
| Agmatine SO$_4$, 0.1% | 204 | 262 | 294 | 226 | 237 |
| Cadaverine.2HCl, 0.1% | 185 | 267 | 306 | 225 | 235 |
| 1,3-Diaminopropane.2HCl, 0.1% | 307 | 397 | 392 | 347 | 317 |
| Putrescine.2HCl, 0.1% | 220 | 370 | 399 | 245 | 236 |
| Spermidine.3HCl, 0.02% | 280 | 392 | 478 | 306 | 333 |
| Spermine.4HCl, 0.02% | 415 | 478 | 478 | 487 | 471 |

It is readily apparent from the consideration of Table 1 that the addition of D- or DL-arginine and D- or DL-ornithine to fermentation medium stimulates the production of cephamycin C. Examples on the stimulation of production of cephamycin C by the polyamine compounds are documented in Table 2. Tables 3, 4 and 5 show the results which demonstrate that the combined addition of an amino acid with a polyamine compound gives rise to greater cephamycin C productivity when compared to the stimulation caused by the separate addition of the compounds. The examples clearly demonstrate that D- or DL-arginine, D- or DL-ornithine, alone or in combination with the polyamines, 1,3-diaminopropane, 1,3-diamino-2-hydroxypropane, N-methyl-1,3-diaminopropane, agmatine, spermidine, spermine, cadaverine and putrescine; or D- or DL-lysine in combination with said polyamines all demonstrate the unexpected phenomenon of stimulating the production of antibiotic cephamycin C.

Any departure from the above description which conforms to the present invention is intended to be included within the scope of the claims.

What is claimed is:

1. In the process for preparing cephamycin C by growing a cephamycin C producing species of Streptomyces in a nutrient medium, the improvement which comprises the addition of the amino acid D- or DL-arginine, D- or DL-ornithine or one of several polyamines selected from the group consisting of 1,3-diaminopropane; 1,3-diamino-2-hydroxypropane; N-methyl-1,3-diaminopropane, agmatine, spermidine, spermine, cadaverine and putrescine to the nutrient medium.

2. The process of claim 1 wherein the Streptomyces specie is *Streptomyces lactamdurans*.

3. The process of claim 2 wherein the nutrient medium is a complex organic nutrient medium.

4. The process of claim 3 wherein the nutrient medium contains from about 0.025 to about 0.40 percent (weight/volume) of the amino acids D- or DL-arginine or D- or DL-ornithine calculated as the hydrochloride; or from about 0.01 to about 0.2% (weight/volume) of 1,3-diaminopropane calculated as the dihydrochloride; or from about 0.0025 to 0.05% (weight/volume) of spermidine or spermine calculated as the trihydrochloride and tetrahydrochloride respectively; or from about 0.025 to 0.2% (weight/volume) of cadaverine or putrescine calculated as the dihydrochloride; or from about 0.025 to 0.2% (weight/volume) of agmatine calculated as the sulfate; or from about 0.05 to about 0.2% (weight/volume) of 1,3-diamino-2-hydroxypropane or N-methyl-1,3-diaminopropane as the free base.

5. In the process for preparing cephamycin C by growing a cephamycin C producing species of Streptomyces in a nutrient medium, the improvement which comprises the addition of the amino acid D- or DL-arginine, D- or DL-ornithine or D- or DL-lysine in combination with a polyamine selected from the group consisting of 1,3-diaminopropane; 1,3-diamino-2-hydroxypropane; N-methyl-1,3-diaminopropane, agmatine, spermidine, spermine, cadaverine and putrescine.

6. The process of claim 5 wherein the Streptomyces species is *Streptomyces lactamdurans*.

7. The process of claim 6 wherein the nutrient medium is a complex organic nutrient medium.

8. The process of claim 7 wherein the nutrient medium contains the amino acids D- or DL-arginine, D- or DL-ornithine or D- or DL-lysine to the extent of about 0.1 to about 0.2% (weight/volume) calculated as the hydrochloride in combination with about 0.1% (weight/volume) of 1,3-diaminopropane or cadaverine or putrescine calculated as the dihydrochloride; or about 0.02% (weight/volume) of spermidine or spermine calculated as the trihydrochloride and tetrahydrochloride respectively; or about 0.1% (weight/volume) agmatine calculated as the sulfate; or about 0.05 to about 0.2% (weight/volume) of 1,3-diamino-2-hydroxypropane or N-methyl-1,3-diaminopropane as the free base.

9. The process according to claim 8 wherein DL-lysine and 1,3-diaminopropane is added to the extent of about 0.1% (weight/volume) calculated as the hydrochloride and dihydrochloride respectively.

* * * * *